United States Patent [19]

Crano

[11] 4,059,655

[45] Nov. 22, 1977

[54] PROCESS FOR PREPARING HALOGENATED DIARYL HYDROGEN PHOSPHATES

[75] Inventor: John C. Crano, Akron, Ohio

[73] Assignee: PPG Industries, Inc., Pittsburgh, Pa.

[21] Appl. No.: 634,690

[22] Filed: Nov. 24, 1975

[51] Int. Cl.² .............................................. C07F 9/09
[52] U.S. Cl. .................................... 260/983; 260/965
[58] Field of Search ........................................ 260/983

[56] References Cited

U.S. PATENT DOCUMENTS

| | | | |
|---|---|---|---|
| 3,155,706 | 11/1964 | Camacho et al. | 260/983 X |
| 3,163,670 | 12/1964 | Rosemund et al. | 260/983 X |
| 3,657,398 | 4/1972 | Ismail | 260/983 |

*Primary Examiner*—Anton H. Sutto
*Attorney, Agent, or Firm*—William M. Dooley; Mark Levin

[57] ABSTRACT

Halogenated diaryl hydrogen phosphates having in admixture only a minor proportion of monoaryl and triaryl phosphates are prepared by selectively hydrolyzing a corresponding triaryl phosphate or by reacting 2,6-dihalophenols having bromine or iodine atoms in the 2 and 6 positions with a phosphorous oxyhalide in the presence of an aromatic tertiary amine or carboxylic acid amide and, preferably, an inert organic solvent to form a mixture of diarylphosphorohalidate and triaryl phosphate and hydrolyzing the mixture.

6 Claims, No Drawings

PROCESS FOR PREPARING HALOGENATED DIARYL HYDROGEN PHOSPHATES

BACKGROUND OF THE INVENTION

1. Field of the Invention

This invention relates to a process for preparing halogenated diaryl hydrogen phosphate esters. More particularly it relates to the hydrolysis of tris(2,6-dihalophenyl) phosphates, and to reaction of certain 2,6-dihalophenols with phosphorous oxyhalide and hydrolysis of the reaction products, to form diaryl hydrogen phosphates having in admixture only a minor proportion of monoaryl and triaryl phosphates.

Halogenated aryl phosphate esters are useful as plasticizers, pesticides, flame retardants, and textile impregnating agents. As flame retardants they may be incorporated into plastic such as polyethylene and polystyrene, or they may be applied to fabrics from solution in water or an organic solvent. Halogenated diaryl hydrogen phosphates are currently of interest both as flame retardants and as intermediates in the preparation of diaryl phosphate derivatives.

2. Description of the Prior Art

The preparation of aryl phosphates by reaction of phenols (ROH) with phosphorous oxyhalides (POX$_3$) and subsequent hydrolysis has long been known. Although the process has been considered satisfactory for the preparation of mixtures of monoaryl, diaryl, and triaryl phosphate esters, it has not been recommended for the production of acceptably pure diaryl hydrogen phosphate because of the difficultly of separating the mixed esters produced by the process. If two moles of a phenol are reacted with one mole of phosphorous oxyhalide and the reaction products are hydrolyzed, the product has been reported to be not primarily the desired diaryl hydrogen phosphate, but rather a mixture of monoaryl, diaryl, and triaryl phosphates together with unreacted phenol. The yield of the desired reaction

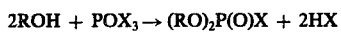
2ROH + POX$_3$ → (RO)$_2$P(O)X + 2HX is diminished by competition from the reactions
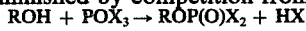
ROH + POX$_3$ → ROP(O)X$_2$ + HX and
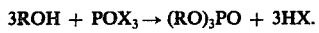
3ROH + POX$_3$ → (RO)$_3$PO + 3HX.

The mixture of products from these reactions is difficult to separate. Hydrolysis of the mixture yields a mixture of esters which is also difficult to separate. The process is said to produce good yields of triaryl phosphate if an excess of the phenol, i.e., more than 3 moles per mole of phosphorus oxyhalide, is used.

A number of methods have been proposed for the preparation of pure diaryl hydrogen phosphates. U.S. Pat. No. 3,019,249 describes the use of an exchange reaction between triaryl phosphate and a selected proportion of phosphoric acid or alkali metal phosphate.

U.S. Pat. No. 3,155,706 relates to the preparation of diarylphosphorohalidates which may be hydrolyzed to form diaryl hydrogen phosphates, by adding, separately and simultaneously, one molecular proportion of phosphorus oxyhalide and one molecular proportion each of an alkali metal hydroxide and an alkali metal phenoxide in aqueous solution to one molecular proportion of a phenol while maintaining the temperature of the reaction mixture between −10° and 20° C. and the pH between 4.0 and 6.9. The need for careful control of rates of addition, temperature, and pH is evident. This patent also states that selective hydrolysis of triaryl phosphate esters to diaryl esters is difficult to control, particularly in acidic conditions, where progressive degradation products down to phosphoric acid generally are formed.

U.S. Pat. No. 3,657,398 shows the preparation of halogenated diaryl phosphates including bis(2,4,6-tribromophenyl) hydrogen phosphate by reaction of a halogen fed phenol with an alkyldichlorophosphate in the presence of a catalyst such as tertiary amine.

U.S. Pat. No. 3,689,602 shows the preparation of halogenated aryl phosphates by reaction of halophenols including 2,4,6-tribromophenol with acid halides of phosphorus, including phosphorus oxychloride, in the presence of a catalyst amount of a tertiary aromatic amine or a carboxylic acid amide.

The cited patents point out shortcomings of the phenol-phosphorus oxyhalide-hydrolysis route to diaryl hydrogen phosphates and emphasize that a mixture of reaction products is obtained.

SUMMARY OF THE INVENTION

It has now been found that certain triaryl phosphates, i.e., tris(2,6-dihalophenyl) phosphates having either bromine or iodine in each of 2 and 6 ring positions of each of the phenyl substitutents, can be converted almost quantitatively to a corresponding bis(2,6-dihalophenyl) hydrogen phosphate by hydrolysis under certain conditions, while minimizing or substantially avoiding coproduction of progressive degradation products, i.e., 2,6-dihalophenyl dihydrogen phosphate and phosphoric acid. Thus, the bis(2,6-dihalophenyl) hydrogen phosphate is produced in a high yield, i.e., at least about 90 mole percent based on the moles of tris(2,6-dihalophenyl) phosphate used.

Furthermore, it has now been found, despite prior art indications to the contrary, that with certain phenols, i.e., 2,6-dihalophenols having either bromine or iodine in each of the 2 and 6 ring positions, it is possible to use the phenol-phosphorus oxyhalide reaction followed by hydrolysis to produce diaryl hydrogen phosphates while maximizing conversion of the phenol to the diaryl phosphate and minimizing or even substantially avoiding coproduction of monoaryl dihydrogen phosphates and triaryl phosphates.

This, in accordance with the present invention, diaryl hydrogen phosphate is produced by reaction of a 2,6-dihalophenol, such as 2,6-dibromophenol, 2-bromo-6-iodophenol, or 2,4,6-tribromophenol, with a phosphorous oxyhalide such as phosphorus oxychloride to form intermediate reaction product and hydrolysis of the reaction product to form a diaryl hydrogen phosphate having in admixture therewith only a minor proportion of monoaryl and triaryl phosphates. Upon recovery without further purification, the diaryl phosphate is pure enough for many purposes even though it may contain small amounts of monoaryl and triaryl phosphates. The diaryl phosphate may be further purified, for example by recrystallization, if even purer product is desired.

The crude aryl phosphate product obtained via the phenol-oxyhalide-hydrolysis route in accordance with the present invention is acceptably pure for practical purposes. Usually the crude aryl phosphate product is at least about 90 weight percent diaryl hydrogen phosphate, and monoaryl and triaryl phosphates are present in the crude product only as impurities in a minor proportion, i.e., a total of less than about 10 weight percent, often much less than 10 weight percent of the total aryl phosphate. Monoaryl dihydrogen phosphate is usually the major impurity. Triaryl phosphate is present, if at all, in very small amounts, i.e., less than 5%. Thus, the crude diaryl phosphate product of the present invention is pure when compared with the mixed products disclosed in the cited patents.

DETAILED DESCRIPTION OF THE INVENTION

The 2,6-dihalophenols useful in the practice of the present invention are those having either bromine or iodine in each of the 2 and 6 ring positions. They may be represented by the structural formula:

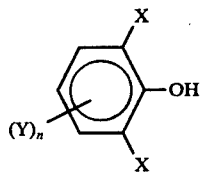

wherein each X independently is bromine or iodine, each Y independently is fluorine, chlorine, bromine, iodine, a lower alkyl or halogenated alkyl group having from 1 to 6 carbons, an aryl or halogenated aryl group having from 6 to 12 carbons, or a nitro group, and $n$ is from 0 to 3. The distinctive characteristic of these phenols is the presence of the large atoms, bromine or iodine, in the 2 and 6 positions, and therefore Y may be any inert substituent, i.e., one that does not interfere with or participate in the phenol-oxyhalide reaction or the hydrolysis reaction. For phenols used in preparing flame retardants, $n$ is preferably 1 to 3 and Y is preferably halogen, particularly bromine.

Useful tris(2,6-dihalophenyl) phosphates are those whose 2,6-dihalophenyl substituents correspond to the useful phenols described above.

It is believed, without intent to be bound by the theory, that steric hindrance of the halogen substituents in the 2 and 6 ring positions on these phenols minimize the formation of triaryl phosphates in the phenol-phosphorus oxyhalide reaction and renders such triaryl phosphates especially sensitive to selective hydrolysis down to the diaryl hydrogen phosphate and the phenol. Thus, the product obtained by the practice of this invention contains little or substantially no triaryl phosphate, and the amount of monoaryl dihydrogen phosphate in the product may be minimized by the use of a small excess of the phenol in the reaction with phosphorus oxyhalide.

The aforementioned beneficial results have been demonstrated with 2,6-dibromophenols, namely 2,4,6-tribromophenol and pentabromophenol, when reacted with phosphorus oxychloride in the presence of benzene and pyridine, as set forth in the Examples and also with 2,4,6-tribromophenol in the presence of toluene and N,N-di-n-butyl benzamide. In addition, tris(2,4,6-tribromophenyl) phosphate has been hydrolyzed almost quantitatively to bis(2,4,6-tribromophenyl) hydrogen phosphate in tetrahydrofuran containing a small concentration of water. For the foregoing reason, the beneficial results are believed to be attainable also with other 2,6-dibromophenols, with phenols, having iodine in place of either or both of the bromines in the 2 and 6 ring positions and with corresponding tris (2,6-dihalophenyl) phosphates. In addition to phosphorus oxychloride, phosphorus oxybromide is deemed useful in the present invention because of its similarity in chemical behavior toward phenols. Similarly, pyridine and N,N-di-n-butyl benzamide are considered representative of aromatic tertiary amines and carboxylic acid amides generally for use in the present invention.

Useful 2,6-dihalophenols include 2,6-dibromophenols such as 2,6-dibromophenol, 2,3,6-tribromophenol, 2,4,6-tribromophenol, 2,3,4,6-tetrabromophenol, 2,3,5,6-tetrabromophenol, pentabromophenol, 2,6-dibromo-4-methylphenol, 2,6-dibromo-4-phenylphenol, 2,6-dibromo-3,4,5-trichlorophenol, 2,6-dibromo-4-nitrophenol, and 2,6-dibromo-3,5-dichlorophenol. The iodine-containing phenols, such as 2,6-diiodophenol, 2,4,6-triiodophenol, 2,6-diiodo-4-chlorophenol, 2-bromo-6-iodophenol, and 2,4-dibromo-6-iodophenol are also expected to be useful in the practice of this invention. Particularly, 2,4,6-tribromophenol is preferred for its usefulness, availability, and ease of preparation. Mixtures of the phenols may be used to provide mixed diaryl phosphates, if desired.

Useful tris(2,6-dihalophenyl) phosphates in addition to tris (2,4,6-tribromophenyl) phosphate include, for example, tris(2,6-dibromophenyl) phosphate, tris(pentabromophenyl) phosphate, tris(2,6-diiodophenyl) phosphate, tris(2,6-dibromo-4-methylphenyl) phosphate, and tris(2-bromo-6-iodophenyl) phosphate. Tris(2,6-dihalophenyl) phosphates containing mixed 2,6-diahlophenyl substituents may also be used, if desired, to produce mixed diaryl hydrogen phosphates.

Useful phosphorus oxyhalides are $POCl_3$ and $POBr_3$. $POCl_3$ is preferred because it is cheap and readily available.

In accordance with this invention, a liquid mixture of a useful 2,6-dihalophenol, a phosphorus oxyhalide, and at least a catalyst amount of an aromatic tertiary amine of a carboxylic acid amide is heated at a temperature of about 50° to about 150° C. until hydrogen halide is evolved. An inert organic solvent such as benzene or hexane may also be present. The reaction products so prepared may then be hydrolyzed to the diaryl hydrogen phosphate, as described below.

In accordance with one embodiment, a useful 2,6-dihalophenol as defined above and a phosphorus oxyhalide are reacted in the presence of an inert organic solvent and an aromatic tertiary amine to form intermediate product, and then hydrolysis of the intermediate product is effected. Hydrolysis produces aryl phosphates of which triaryl phosphate constitutes only a minor proportion. Thus the use of a contemplated phenol minimizes the coproduction of triaryl phosphate. Preferably, the 2,6-dihalophenol is employed in small excess in order to minimize formation of monoarylphosphorodichloridate and therefore minimize coproduction of monoaryl phosphate, and the aromatic tertiary amine is used in a substantial amount in order to remove hydrogen halide as it is formed. In accordance with the present invention, when an excess of a contemplated phenol is used, an aryl phosphate product is obtained upon hydrolysis, of which diaryl phosphate constitutes a major proportion, i.e., at least about 90 weight percent, and monoaryl and triaryl phosphates together constitute a minor proportion, i.e., less than about 10 weight percent.

The available evidence indicates that the intermediate product of the phenol-oxyhalide reaction is a mixture of a major proportion of diarylphosphorohalidate, a lesser proportion of triaryl phosphate, and a minor proportion of monoarylphosphorodihalidate. Also present with the intermediate product are the inert organic solvent and aromatic tertiary amine hydrogen halide, which is produced in the course of the phenoloxyhalide reaction.

Inert organic solvents in addition to benzene and toluene which would be useful in the practice of this invention include aliphatic and aromatic hydrocarbons and mixtures thereof, and open-chain and cyclic ethers, such as chlorobenzene, nitrobenzene, toluence, xylene, hexane, octane, isopropyl ether, isoamyl ether, 1,4-dioxane, and diphenyl ether. Preferably, solvents are used in which the products of the reaction between the phenol and the phosphorus oxyhalide (primarily diarylphosphorohalidate and triaryl phosphate) are soluble, and in which the tertiary amine hydrogen halide and the diaryl hydrogen phosphate are both insoluble. This allows easy removal of the tertiary amine hydrogen halide from the product mixture before hydrolysis, and easy recovery of the diaryl hydrogen phosphate after hydrolysis. Such preferred solvents would include benzene, toluene, chlorobenzene, hexane, heptane, carbon tetrachloride, and mixtures of aliphatic and aromatic solvents such as mixtures of heptane and benzene, depending upon the phenol, the phosphorus oxyhalide, and the tertiary amine employed. For example, benzene is preferred for use in the preparation of bis(2,4,6-tribromophenyl) hydrogen phosphate, as seen in Examples I and II.

Sufficient solvent should be used to provide an easily worked reaction mixture. It is desirable but not necessary to dissolve all of the 2,6-dihalophenol in solvent before adding the phosphorus oxyhalide and the tertiary amine. It is convenient to use the minimum amount of solvent needed to dissolve substantially all of the phosphorus reaction products while dissolving little or substantially no tertiary amine hydrogen halide. The terms "soluble" and "insoluble" are not absolute but refer, of course, to degrees of solubility and insolubility ordinarily considered sufficient to allow separation of compounds by methods such as recrystallization or solvent extraction. Where phosphorus oxychloride is used as a reagent, the choice of a preferred solvent will depend primarily on the solubility of the 2,6-dihalophenol and its corresponding phosphates and phosphorochloridates. Most common aromatic tertiary amines exhibit the desirable solubility behavior in the named solvents.

Aromatic tertiary amines in addition to pyridine which would be useful in the practice of this invention are amines in which the nitrogen is part of an aromatic ring, such as isoquinoline, pyrazine, oxazine, quinazoline, benzothiazole, oxadiazole, and oxazole. Amines which are soluble in the chosen solvent and whose hydrogen halide salts are insoluble are preferred.

Carboxylic acid amides, in addition to N,N-di-n-butyl benzamide, which would be useful include amides of monobasic and dibasic aliphatic and aromatic, saturated and unsaturated carboxylic acids having 1 to 20 carbons and ammonia, monoamines and diamines where the N-substituents are aliphatic or aromatic groups having 1 to 20 carbons. Useful carboxylic acid amides include, for example, dimethylacetamide, N-benzylbutyric acid amide, formamide, N,N-di-n-propyl butyric acid amide, acetoacetic acid anilide, benzoic acid benzylamide, N,N-dimethylbenzoic acid amide, and N,N'-diformylhexamethylenediamine.

In general, those aromatic tertiary amines and carboxylic acid amides may be used which are disclosed in U.S. Pat. No. 3,689,602, column 3, line 50 to column 5, line 7, herein incorporated by reference.

Ordinarily, when diaryl phosphate is desired, the 2,6-dihalophenol and the phosphorus oxyhalide are employed in about the stoichiometric ratio of 2 to 1. If the presence of greater amounts of monoaryl phosphate in the diaryl product is acceptable, smaller ratios may be used. If very low ratios are used, e.g., 1 to 1, monoaryl phosphate may predominate in the hydrolyzed product. If ratios approaching 2 to 1 are used, then diaryl phosphate will predominate and a lesser proportion of monoaryl phosphate will be present. In either case, the amount of triaryl phosphate produced will be a minor proportion of the total phosphate. A lesser proportion is defined to be less than about 50 weight percent. A minor proportion is defined to be less than about 10 weight percent. However, in order to minimize the amount of monoaryl phosphate in the product, a small excess of the 2,6-dihalophenol may be used. The ratio is preferably from about 2.1 to 1 to about 2.5 to 1. Greater ratios, up to 3 to 1 or even 4 to 1 or more may be used. With the larger ratios, the formation of a major proportion of triaryl phosphate would ordinarily be expected in view of the disclosures triaryl phosphate would ordinarily be expected in view of the disclosures in the cited patents. However, it has been observed that even when ratios of up to 4 to 1 are used, the intermediate product mixture contains substantially more diarylphosphorohalidate than triaryl phosphate. This observation further supports the view that steric hindrance in the triaryl phosphate is significant.

The aromatic teritiary amine or carboxylic acid amide may be used in widely varying amounts. A catalytic amount, i.e., between about 0.001 and 0.1 or more moles per mole of phosphorus oxyhalide, may be used. When a catalytic concentration of amine or amide is used, it is desirable to bubble nitrogen through the reaction mixture to sweep out hydrogen halide. Alternatively, a substantial amount of aromatic tertiary amine, up to about 2.1 moles or more per mole of phosphorus oxyhalide may be used both to catalyze the reaction and to take up hydrogen halide to form amine salt. Lesser substantial amounts e.g., about 1 mole per mole, may be used in combination with nitrogen sweep if desired.

Reaction may proceed slowly at room temperature when the dihalophenol, inert solvent, phosphorus oxyhalide, and aromatic tertiary amine or carboxylic acid amide are mixed. The reaction mixture may be heated to speed the reaction. Temperatures of between about 30° and 150° C. are useful. Preferably, the mixture is heated to between about 50° and 90° C. Temperatures between about 50° C. and the reflux temperature of the mixture are generally satisfactory. Heating may continue for from about 30 minutes to about 4 hours or more. Generally, 1 to 3 hours of heating will be sufficient. After heating is discontinued, the mixture may be allowed to cool to room temperature and, preferably, stirring may be continued for about 1 to 6 hours or more, e.g., overnight. The reaction is conducted in liquid medium, but small amounts of undissolved reagent may be present. Furthermore, as the reaction proceeds, reaction products and amine salts may precipitate. Nevertheless, the reaction mixture is at least initially primarily in the liquid phase, and temperatures and pressures consistent with that state may be employed.

If the hydrogen halide salt of the tertiary amine is insoluble in the chosen inert organic solvent, amine salt precipitates as the reaction proceeds, and may easily be removed by filtration or by extraction with water. Water may then be added directly to the remaining mixture of reaction products in order to effect hydrolysis to form the diaryl hydrogen phosphate. If desired, hydrolysis may be carried out while the tertiary amine salt is present.

As described above, the contemplated 2,6-dihalophenols react with phosphorus oxyhalide to produce primarily a mixture of diarylphosphorohalidate and triaryl phosphate and a minor proportion of monoarylphosphorodihalidate. It has been found that a contemplated tris(2,6-dihaloaryl) phosphate, e.g., tris(2,4,6-tribromophenyl) phosphate, may be converted almost quantitatively to the corresponding diaryl hydrogen phosphate, e.g., bis(2,4,6-tribromophenyl) hydrogen phosphate, by hydrolysis under certain conditions. Furthermore, under the same conditions, a mixture of diarylphosphorohalidate and triaryl phosphate such as that produced by the reaction of a contemplated 2,6-dihalophenol with a phosphorus oxyhalide may also be converted to the corresponding diaryl hydrogen phosphate with little or no progressive degradation of the diaryl phosphate.

Hydrolysis of a contemplated tris(2,6-dihalophenyl) phosphate or of a mixture of a bis(2,6-dihalophenyl) phosphorohalidate and a tris (2,6-dihalophenyl) phosphate may be effected by reacting the phosphate or mixture with water in the presence of an inert organic hydrolysis solvent such as benzene or tetrahydrofuran in liquid reaction medium. The temperature may be between about room temperature, i.e., 20° C., and 100° C. At about 20° C., 12 to 18 hours of stirring is usually required, but at higher temperatures, about 50° to 100° C., 15 minutes to 5 hours will be sufficient. Within these ranges, the shorter times and moderate temperatures are preferred to achieve a reasonable rate of hydrolysis without substantial degradation of the desired diaryl hydrogen phosphate. Temperatures of between about 65° and 85° C. and times between about 1 and 5 hours are preferred.

The organic solvent used for the hydrolysis is preferably one in which the diaryl hydrogen phosphate is insoluble and the triaryl phosphate and the diarylphosphorohalidate are soluble. The diaryl hydrogen phosphate will then precipitate as it is formed and will be safer from progressive degradation. This consideration is of greater importance when the hydrolysis is carried out at the higher temperatures, i.e., between about 50° and 100° C. The solvents preferred for use with the phenol-oxyhalide reaction are also preferred for use in the hydrolysis, notably benzene and toluene. An inert solvent is one which does not inhibit or otherwise interfere with the desired hydrolysis reaction.

The pH of the hydrolysis mixture may vary from about 1 to 9, preferably below about 7. As hydrolysis proceeds, the pH of the mixture will drop, and mixtures of triaryl phosphate and diarylphosphorohalidate produced by the phenol-oxyhalide reaction will generally be acidic. The addition of water alone, without added acid or base, is sufficient to effect hydrolysis in accordance with this invention. The pH may be regulated during hydrolysis, if desired, but regulation is unnecessary so long as the pH is lower than about 10. Strongly alkaline pH above about 10 may permit excessive degradation of the desired diaryl hydrogen phosphate.

Although U.S. Pat. No. 3,155,706 discloses that diarylphoshorohalidates may be hydrolyzed to diaryl hydrogen phosphates under conditions similar to those described here, it was surprising that the tris(2,6-dihalophenyl) phosphates disclosed herein are hydrolyzed selectively to the bis(2,6-dihalophenyl) hydrogen phosphates under the same mild conditions. Thus, in accordance with the present invention there is provided a simple, reliable method for preparing certain bis(2,6-dihalophenyl) hydrogen phosphates from certain 2,6-dihalophenols and phosphorus oxyhalides, or directly from the tris(2,6-dihalophenyl) phosphate, using controlled hydrolysis of the tris phosphate or of the phenol-oxyhalide reaction product mixture while minimizing coproduction of monoaryl and triaryl phosphates.

From nuclear magnetic resonance spectra, it appears that the triaryl phosphate is hydrolyzed almost quantitatively to diaryl hydrogen phosphate and to the 2,6-dihalophenol. The phenol is easily separated from the phosphate mixture by conventional methods such as recrystallization or filtration using common solvents such as water, benzene, or ethanol, leaving the diaryl hydrogen phosphate reasonably pure without need for further purification. Of course, if even more pure product is desired, the diaryl hydrogen phosphate may be recrystallized from a suitable solvent or mixture of solvents such as tetrahydrofuran and methyl alcohol, depending on the phosphate being made.

The following examples will serve to illustrate the practice of the present invention.

EXAMPLE I

A three-necked, round-bottomed 2000 milliliter flask was equipped with magnetic stirrer, thermometer, and pressure-equalizing dropping funnel, and immersed in a room temperature water bath. The flask was charged with 700 milliliters of benzene, 150 grams (0.45 mole) of 2,4,6-tribromophenol, and 30.8 grams (0.20 mole) of phosphorus oxychloride. The mole ratio of 2,4,6-tribromophenol to phosphorus oxychloride was 2.25 to 1. Over a period of 0.5 hour, 34.6 grams (0.44 mole) of pyridine was added from the dropping funnel wwith slight evolution of heat. The mixture was stirred at room temperature for 4.5 hours, refluxed at 84° C. for 1.5 hours, and then allowed to cool and stir overnight. The mixture was then filtered, and the filtrate was combined with 200 milliliters of water. The mixture was stirred and refluxed at 75° C. for 5 hours, cooled, and stirred overnight. A large amount of white solid was filtered from the reaction mixture and dried overnight under vacuum in the presence of phosphorus pentoxide, yielding 133 grams of crude bis (2,4,6-tribromophenyl) hydrogen phosphate.

The water-benzene filtrate was stripped on a rotary evaporator to remove benzene, and filtered again, giving 30.6 grams of a tan solid, shown by its spectra to be 2,4,6-tribromophenol. Thus a substantial portion of unused starting material may be recovered easily for reuse.

The crude product was heated to 80°–90° C. under vacuum for 2 hours and cooled under vacuum, losing 6.2 percent of its weight. Yield was 86 percent based on 125 grams of dried crude product. The melting point was 236°–239° C. (reported value: 235°–238° C.). This dried crude product was subjected to elemental analysis by X-ray spectroscopy, with the following results:

|  | Br | P |
|---|---|---|
| Calculated for $C_{12}H_5Br_6O_4P$ | 66.29 | 4.28 |
| Found | 64.02 | 4.49 |

These figures indicate that the bromine content of the crude product is slightly low, and the phosphorus content slightly high with respect to the values calculated for pure bis(2,4,6-tribromophenyl) hydrogen phosphate. This is consistent with the presence of at most a very small amount of tris(2,4,6-tribromophenyl) phosphate and with the presence of only a minor amount of 2,4,6-tribromophenyl dihydrogen phosphate.

EXAMPLE II

The procedure of Example I was modified slightly to produce an even purer product.

Using the same apparatus, the flask was charged with 800 milliliters of benzene and 160 grams (0.48 mole) of 2,4,6-tribromophenol was dissolved completely in the benzene. Then 32.8 grams (0.21 mole) of phosphorous oxychloride was added. The ratio of 2,4,6-tribromophenol to phosphorus oxychloride was 2.28 to 1. The dropping funnel was charged with 37.0 grams (0.47 mole) of pyridine and 15 milliliters of benzene; the mixture was added to the flask over a period of about 20 minutes. The temperature in the flask rose slightly to 25°-28° C. The mixture was stirred for 4 hours and then heated to 65° C. over a period of 45 minutes. Heating was then stopped and the mixture was stirred overnight.

The mixture was filtered, giving 49.0 grams (0.42 mole) of pyridine hydrochloride. The filtrate was refluxed with 200 milliliters of water for 2.0 hours at 75° C. and allowed to cool. The yield was 93.0 grams (58 percent of theoretical) of dried crude bis(2,4,6-tribromophenyl) hydrogen phosphate having a melting point of 243°-245° C., 6° to 7° C. higher than that of the crude product of Example I.

Elemental analysis by X-ray spectroscopy gave the following results:

|  | Br | P |
|---|---|---|
| Calculated for $C_{12}H_5Br_6O_4P$ | 66.29 | 4.28 |
| Found, Example II | 65.6 | 4.4 |
| Found, Example I | 64.02 | 4.49 |

Note that in the product in this Example, the bromine content and the phosphorous content are both closer to the calculated values. It is believed that the higher purity of the product in this Example was due to the shorter time of the hydrolysis step (2hours instead of 5) and that the higher yield of Example I was due to the more vigorous conditions of the first step (1.5 hours reflux at 84° C. instead of 45 minutes at 65° C.).

EXAMPLE III

A 300 milliliter, three-necked flask was charged with 150 milliliters of benzene, 48.9 L grams (0.01 mole) of pentabromophenol, and 6.8 grams (0.047 mole) of phosphorus oxychloride. The phenol did not dissolve completely. From a dropping funnel, 7.7 grams (0.097 mole) of pyridine in 10 milliters of benzene was added over a 10 minute period at 20°-22° C. The mixture was refluxed at 79° C. for 6 hours, cooled to room temperature, and filtered. The residue was dried in a vacuum oven and then stirred for 18 hours with 500 milliliters of water to extract pyridine hydrochloride, filtered, and dried in a vacuum oven at 60° C. over Drierite for 3 hours to give 45.0 grams to solid. A 10.0 gram portion of the dried solid was stirred and refluxed with 200 milliliters of tetrahydrofuran and 5.0 milliliters of water for 1 hour, and filtered. The residue was dried, giving 4.8 grams of gray solid melting at 335° C. The solid was identified as bis(pentabromophenyl) hydrogen phosphate through its mass spectrum and elemental analysis.

Elemental anaylsis gave the following results:

|  | Br | P |
|---|---|---|
| Calculated for $C_{12}HBr_{10}O_4P$ | 76.9 | 2.98 |
| Found | 77.4 | 2.54 |

Although the present invention has been described with reference to specific details of particular embodiments, the specifics are not intended to limit the invention except insofar as they appear in the following claims.

I claim:

1. In the method for preparing a halogenated diaryl hydrogen phosphate which comprises reacting a halogenated phenol with a phosphorus oxyhalide in the presence of a catalyst and an inert organic solvent, the phenol being employed in excess of 2 moles per mole of oxyhalide, to form intermediate reaction product mixture consisting of diaryl phosphorohalidate, triaryl phosphate, and a minor proportion of monoaryl phosphorodihalidate, and then effecting hydrolysis of intermediate reaction product with water to form a final product mixture of diaryl hydrogen phosphate, triaryl phosphate, and a minor proportion of monoaryl dihydrogen phosphate, the improvement for substantially avoiding coproduction of triaryl phosphate in the final product mixture which comprises:

employing as the halogenated phenol a 2,6-dihalophenol having the halogens in its 2 and 6 ring positions selected independently from the group consisting of bromine and iodine, and effecting the hydrolysis in the presence of inert organic hydrolysis solvent at a pH between about 1 and 9 and a temperature between about 20° and 100° C. for a time between about 15 minutes and 18 hours to form bis(2,6-dihalophenyl) hydrogen phosphate having in admixture therewith only a minor proportion of tris(2,6-dihalophenyl)phosphate and 2,6-dihalophenyl dihydrogen phosphate.

2. The method of claim 1, wherein the hydrolysis is effected at a pH between about 1 and 7 and a temperature between about 65° and 85° C. for a time between about 1 and 5 hours.

3. The method of claim 1, wherein the 2,6-dihalophenol is a 2,6-dibromophenol.

4. The method of claim 3, wherein the 2,6-dibromophenol is 2,4,6-tribromophenol, whereby bis(2,4,6-tribromophenyl) hydrogen phosphate is prepared.

5. The method of claim 4, wherein the phosphorus oxyhalide is phosphorus oxychloride, the catalyst is an aromatic tertiary amine employed in a ratio of at least about 2 moles per mole of phosphorus oxychloride, aromatic tertiary amine hydrochloride being formed in the course of the reaction, and the inert organic solvent is one in which intermediate reaction product is soluble but in which the aromatic tertiary amine hydrochloride and the bis(2,4,6-tribromophenyl) hydrogen phosphate are insoluble.

6. The method of claim 5, wherein the aromatic tertiary amine is pyridine, the inert organic solvent is benzene, and the hydrolysis is effected by adding water to a solution of intermediate reaction product in benzene after removing aromatic tertiary amine hydrochloride.

* * * * *

UNITED STATES PATENT OFFICE
CERTIFICATE OF CORRECTION

PATENT NO. : 4,059,655

DATED : November 22, 1977

INVENTOR(S) : John C. Crano

It is certified that error appears in the above-identified patent and that said Letters Patent are hereby corrected as shown below:

Column 10, line 27, Claim 1, "mixture" should be before "with".

Column 10, line 39 Claim 1, --C-- should be after "20°".

Column 10, line 47, Claim 2, --C-- should be after "65°".

Signed and Sealed this

Twenty-first Day of November 1978

[SEAL]

Attest:

RUTH C. MASON
Attesting Officer

DONALD W. BANNER
Commissioner of Patents and Trademarks